(12) United States Patent
Bell et al.

(10) Patent No.: US 6,366,793 B1
(45) Date of Patent: Apr. 2, 2002

(54) MINIMALLY INVASIVE METHODS FOR MEASURING ANALTES IN VIVO

(75) Inventors: Michael L. Bell, Fullerton; Jack D. McNeal, Long Beach, both of CA (US)

(73) Assignee: Beckman Coulter, Inc., Fullerton, CA (US)

( * ) Notice: Subject to any disclaimer, the term of this patent is extended or adjusted under 35 U.S.C. 154(b) by 0 days.

(21) Appl. No.: 09/393,738

(22) Filed: Sep. 10, 1999

(51) Int. Cl.$^7$ .............................. A61B 5/00; G01N 33/53
(52) U.S. Cl. ..................... 600/317; 600/312; 436/501; 436/800; 422/68.1; 422/82.08
(58) Field of Search ..................... 600/309, 310, 600/312, 317, 322, 347, 365; 436/68, 95, 501, 800; 422/68.1, 82.08

(56) References Cited

U.S. PATENT DOCUMENTS

| | | | |
|---|---|---|---|
| 5,342,789 A | * 8/1994 | Chick et al. | 600/322 |
| 5,628,310 A | * 5/1997 | Rao et al. | 600/317 |
| 5,747,349 A | 5/1998 | Van den Engh et al. | 436/172 |
| 6,002,954 A | * 12/1999 | Van Antwerp et al. | 600/317 |
| 6,011,984 A | * 1/2000 | Van Antwerp et al. | 600/317 |

OTHER PUBLICATIONS

James, Tony D., et al; "Novel Saccharide–Photoinduced Electron Transfer Sensors Based on the Interaction of Boronic acid and Amine"; *J. Am. Chem. Soc.* vol. 117, pp. 8982–8987 (1995).

Abstract—McShane, Michael J., et al; AA (Texas A&M Univ.) Publication: Proc. SPIE vol. 3599, p. 93–100, Optical Diagnostics of Biological Fluids IV, Alexander V. Priezzhev; Toshimitsu Asakura Publication Date: May 1999.

* cited by examiner

*Primary Examiner*—Eric F. Winakur
(74) *Attorney, Agent, or Firm*—William H. May; Arnold Grant; Sheldon & Mak

(57) ABSTRACT

Minimally invasive methods for measuring an analyte, such as glucose, contained in tile interstitial fluid of a body are provided. The methods include the steps of.

(a) providing at least one sensor particle capable of generating a detectable analyte signal in responding to the analyte concentration of the body, (b) placing the sensor particle into the skin of the body for allowing the sensor particle to be in contact with the interstitial fluid of the body to generate the detectable analyte signal, (c) detecting the generated analyte signal, and (d) determining the concentration of the analyte contained in the interstitial fluid.

The sensor particles may be made to be responsive to an analyte such as glucose concentration contained in a body fluid by including a photo-induced electron transfer receptor specific for the analyte in the sensor particle.

31 Claims, 3 Drawing Sheets

FLUO OF DIBORONIC ACID IN GLUCOSE SERUM
(GOAT SERUM + PBS)

MINIMALLY INVASIVE METHODS FOR MEASURING ANALTES IN VIVO

BACKGROUND OF THE INVENTION

1. Area of the Art

The invention relates generally to methods of measuring an analyte contained in a body fluid and specifically to minimally invasive methods for measuring analytes, particularly glucose contained in an interstitial fluid of a body.

2. Description of the Prior Art

Treatment of diabetes requires frequent measurement of tissue glucose concentration. This is commonly accomplished by drawing a small blood sample (as by a fingerstick) several times daily. A patient typically uses a lancet to draw a droplet of blood and applies the droplet to a reagent strip which is read in a small meter. Obviously, the process is painful, invasive, time-consuming, and generally unpleasant.

Extensive efforts have been made to measure blood glucose non-invasively. However, proposed non-invasive methods, to date, rely on intensive signal massaging to extract a glucose signature from an overwhelming background. Therefore, it appears very difficult to provide a non-invasive measurement with the required specificity, accuracy, and precision.

The methods provided by the present invention provide a compromise between the conventional fingerstick techniques and the prospective non-invasive techniques. Methods of the present invention are able to preserve the diagnostic performance of more intrusive measurements without drawing samples but do require periodic replacement of passive implanted sensors.

SUMMARY OF THE INVENTION

It is an object of the present invention to develop an in vivo glucose measurement method that is as non-invasive as possible. It is also an object of the present invention to provide anin vivo glucose measurement that meets the clinically required specificity, accuracy, and precision. Accordingly, the present invention provides a method for detecting an analyte contained in the interstitial fluid of a body. The method comprises the steps of:

(a) providing at least one sensor particle capable of generating a detectable analyte signal in responding to the analyte concentration in the body, (b) placing the sensor particle into the skin of the body for allowing the sensor particle to be in contact with the interstitial fluid of the body to generate a detectable analyte signal, (c) detecting the generated analyte signal, and (d) determining the concentration of the analyte contained in the interstitial fluid.

Methods of the present invention may be used to measure the glucose concentration of the interstitial fluid in a human as a surrogate measurement for blood glucose. Preferably, the sensor particles are also capable of generating a detectable reference signal for background corrections.

In one embodiment of the present invention, the sensor particles comprise a receptor with a signal fluor. The receptor preferentially recognizes the target analyte, and the binding of the receptor to the analyte allows the signal fluor to generate a detectable analyte signal that is responsive to the concentration of the analyte. A reference fluor may be present in the sensor particles.

Methods of the present invention are less intrusive than the conventional fingerstick technique for measuring blood glucose. They only require periodical replacement of the sensor particles in the skin. In addition, since the sensor particles are in contact with the analytes, relatively specific chemical interactions may be used. The present invention therefore provides better performance than the proposed non-invasive methods for measuring blood glucose. The non-invasive methods rely on intensive signal massaging to extract a glucose signature from an overwhelming background.

The invention is defined in its fullest scope in the appended claims and is described below in its preferred embodiments.

DESCRIPTION OF THE FIGURES

The above-mentioned and other features of this invention and the manner of obtaining them will become more apparent, and will be best understood, by reference to the following description, taken in conjunction with the accompanying drawings. These drawings depict only a typical embodiment of the invention and do not therefore limit its scope. They serve to add specificity and detail, in which.

DETAILED DESCRIPTION OF THE INVENTION

Figure 1:
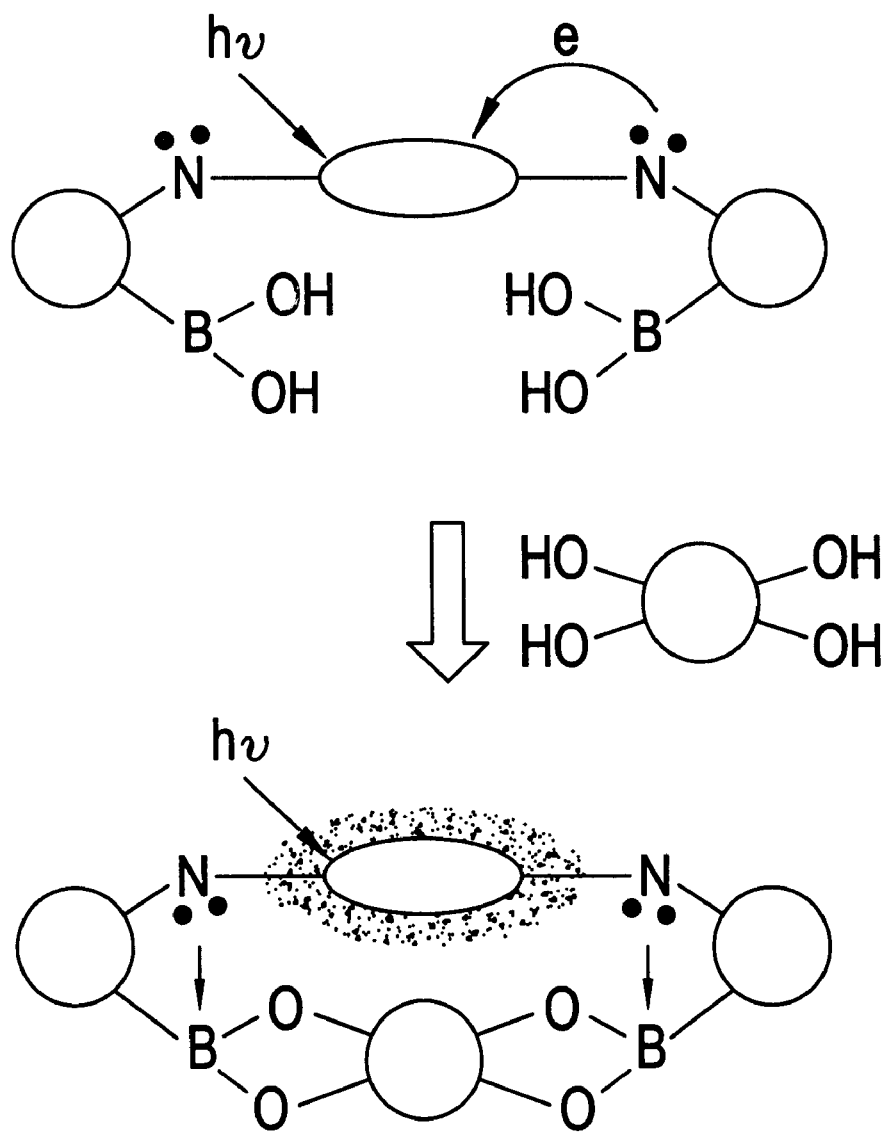
FIG. 1 is a cartoon of the receptor molecules that are used in the present invention.

The present invention provides a method for detecting an analyte contained in the interstitial fluid of a body. The method comprises the steps of:

(a) providing at least one sensor particle capable of generating a detectable analyte signal in responding to the analyte concentration of the body, (b) placing the sensor particle into the skin of the body for allowing the sensor particle to be in contact with the interstitial fluid of the body to generate the detectable analyte signal, (c) detecting the generated analyte signal, and (d) determining the concentration of the analyte contained in the interstitial fluid.

In accordance with one embodiment of the present invention, the analyte may be a glucose, and the concentration of the glucose in the interstitial fluid is determined as a measurement for the glucose concentration in the blood of the human. Glucose within the interstitial fluid is in equilibrium with blood glucose Although there is a time lag of a few minutes before changes in blood glucose concentration are reflected in the interstitial fluid, this lag is negligible compared to the usual time between measurements. Thus, measurement of interstitial fluid glucose may be an adequate surrogate for measurement of capillary blood glucose.

For the purpose of the present invention, a body may be a body of a vertebrate animal. Examples of such an animal include but are not limited to: human; livestock such as cows, goats, sheep, chickens, etc.; and laboratory research animals such as rats, mice, rabbits, monkeys, etc. Preferably, the body is a human body.

In accordance with embodiments of the present invention, a detectable analyte signal may be an optically detectable signal. Preferably, the detectable signals are fluorescence signals. Most preferably, signal fluors contained in a sensor particle of the present invention emit in the near infrared (IR) and are relatively resistant to photo-bleaching. Near IR wavelengths are less readily absorbed or scattered by tissue.

In one embodiment of the present invention, a sensor particle may comprise a particle substrate bound to a receptor with a signal fluor. The receptor preferentially recognizes the analyte, and the binding of the receptor to the analyte allows the signal fluor to generate a detectable analyte signal that is responsive to the concentration of the analyte. The phrase "preferentially recognize" as used herein means that the receptor has a sufficiently higher affinity to the analyte than to other molecules of appreciable concentration contained in the interstitial fluid. The affinity is sufficiently higher if the signal due to binding of other molecules is negligible compared to the signal due to binding of the analyte. When the analyte is glucose, selectivity of a receptor is important but not crucial, since glucose is present at much higher concentration than potentially interfering saccharides.

It should be understood that the sufficiency of the affinity is determined by comparing the receptor affinity of an analyte to that of other molecules contained in a sample. Therefore, in some cases, a receptor that is capable of binding to different molecules with different affinities and that has relatively low affinity to an analyte may also be suitable for the purpose of the present invention, if the analyte is the only molecule that binds to the receptor and that has significant variation in its concentration in a sample. Therefore the bulk of the change in signal may be attributed to changes in analyte concentration, and the concentration of analyte may be determined once a baseline calibration is made.

Sensor particles that contain a collection of lower specificity receptors with distinguishable fluorescence may also be used. Each lower specificity receptor responds to binding of one or more molecular species with different affinities. At least one lower specificity receptor must respond to binding of an analyte. If there are at least as many types of lower specificity receptors as there are molecular species with significant binding, the concentration of analyte may be calculated from the measured signals from each type of lower specificity receptor, and from a priori knowledge of the relative affinities of the lower specificity receptors for the different molecular species. This requires that the signals from each type of lower specificity receptor be distinguishable from one another. In accordance with embodiments of the present invention, the signals may be distinguished by variations in optical properties of the signals. For example, if the signals are fluorescent, the optical property differences may be in emission wavelength, in excitation wavelength, in fluorescence lifetime, in polarization, in phase, or in combinations thereof.

For the purpose of the present invention, preferably, the binding of the receptor to the analyte is reversible so that it may approach an equilibrium value and respond to changes in analyte concentration.

According to one embodiment of the present invention, the sensor particle is also capable of generating one or more detectable reference signals that are distinguishable from the analyte signal. A reference signal may be distinguished from the analyte signal by optical properties. When the signals are fluorescent, the optical property differences may be in emission wavelength, in excitation wavelength, in fluorescence lifetime, in polarization, in phase, or in combinations thereof. Reference signals may be used to correct for variations in illuminating intensity and uniformity, illuminated area, overlying tissue optical density, fluor aging, and the like. Therefore, by comparing the analyte signal to the reference signal, one may correctly determine the concentration of the analyte contained in the interstitial fluid. It should be understood that reference signals may also encode information about the analyte concentration so that the concentration may be determined by combination of the analyte and reference signals or of their measurements.

The sensor particles may be made responsive to analyte concentration by incorporating specific analyte receptors with signal fluors, either onto the surface or into the body of the particles. In accordance with one embodiment of the present invention, when an analyte is glucose, analyte receptors of the present invention may be dual diboronic acids conjugated to fluors, preferably where the fluors have excitation wavelength in the near infrared region (greater than 600 nm). Examples of such dual diboronic acids include, not are not limited to, N,N'-Bis(2-boronylbenzyl)-3,3,3',3'-tetramethylindolinium chloride and 9,10-Bis[N-methyl-M-(o-boronobenzyl)amino]methyl]anthracene.

Examples of a receptor that preferentially recognizes a glucose analyte are also described by Tony James et al., in the *Journal of the American chemical Society*, 1995, vol. 117 pp. 8982–8987, the relevant content of which is incorporated herein by reference. Briefly, these receptors use photo-induced electron transfer (PET) between an amine group and an incorporated anthracene fluor as modulated by binding of saccharide hydroxyls to a pair of boronic acids. The dual boronates confer a tenfold specificity to D-glucose as compared to D-fructose.

Figure 2:
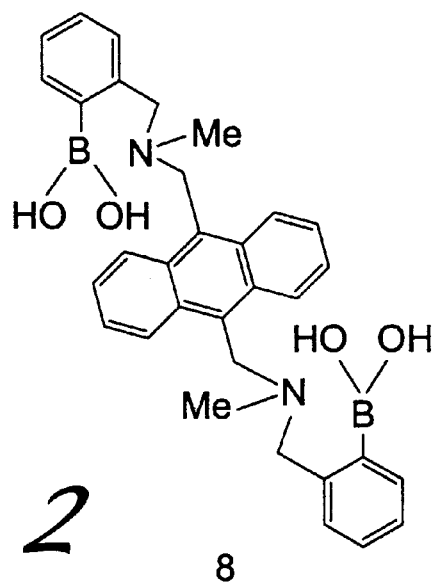
FIG. 2 shows the detailed structure of a glucose receptor molecule of the present invention.
Figure 3:
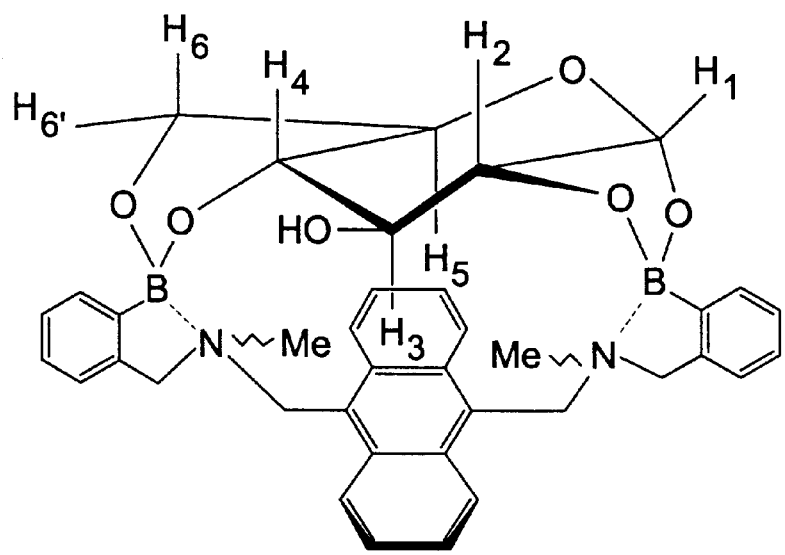
FIG. 3 shows the interaction of the receptor of FIG. 2 with glucose.

FIG. 1 is a cartoon of a receptor molecule with a signal fluor adapted from the reference by Dr. Tony James. It shows: analyte binding groups, comprising spaced dual phenyl boronic acids conferring specificity for α-D-glucopyranose (glucose); a fluorescent group, coupled to the binding groups; and nitrogen atoms, with associated lone pair electrons coupled to the fluorescent group. In the absence of glucose binding (upper portion of figure), the fluorescence by the fluorescent group is quenched. When glucose is bound (lower portion), fluorescence is enhanced. The detailed structure of the glucose receptor molecule, as described in the reference by Tony James, is shown in FIG. 2. FIG. 3 shows the interaction of the receptor of FIG. 2 with glucose as described in the reference by Tony James.

The analyte signal and the reference signal may be generated by the same molecule or by different molecules contained in or on the sensor particles. In one embodiment, the sensor particle contains a receptor with both a signal fluor and a reference fluor. The receptor preferentially recognizes the analyte. When the receptor is bound to the analyte, the signal fluor will generate a detectable signal that is responsive to the concentration of the analyte contained in the interstitial fluid. However, the signal generated by the reference fluor will not be affected by the binding of the receptor to the analyte.

Alternatively, a receptor with one signal fluor may be used. The signal fluor is responsive to the binding of the receptor to an analyte. In this case, the receptor that is bound to the analyte is a bound receptor and the receptor that is not bound to the analyte is a free receptor. The signal fluor generates a first signal when it is contained in a bound receptor. It generates a second signal when it is contained in a free receptor. The first and second signals are distinguishable in their optical properties. In this case, the reference signal, the second signal, also encodes information about the analyte concentration. Both signals are responsive to the concentration of the analyte contained in the interstitial fluid, as the relative distribution of bound and free receptors is controlled by a chemical equilibrium governed by the analyte concentration. Measurements of these two signals may be mathematically combined to deterinine analyte concentration that, except for random fluctuations, is independent of the excitation light level, the optical transmission path, and the absolute number or activity of the sensor particles. A necessary condition for this to occur is for the sensor particles to not significantly alter the concentration of analyte in the interstitial fluid. This may be accomplished by keeping the number of bound receptors small compared to the number of analyte molecules. This condition is easily achieved for analytes of reasonable concentration.

In a different embodiment, the sensor particle may include a first substance capable of generating a signal that is responsive to the analyte concentration of a body and a second substance capable of generating a reference signal that is independent of the analyte concentration of a body. In other words, the reference fluor may be a separate molecule as to the signal fluor that is responsive to the analyte concentration. For example, the first substance may be a receptor which preferentially recognizes the analyte, and the second substance may be a fluorescent molecule that is not capable of binding to a receptor. Examples of such a fluorescent molecule include, but are not limited to, oxazine 750, IR140, IR143 and IR144, all of which are commercially available from Exciton Inc. of Dayton Ohio; Cy2, Cy3, Cy3.5, Cy5, Cy5.5 and Cy7, all of which are commercially available from Amersham Pharmacia Biotech of Sweden and the United Kingdom. Additional examples of fluorescent molecules include phthallocyanine dyes, LaJolla Blue (Si phthallocyanine with PEG axial ligands), fluorescein isothiocyanate ("FITC"), rhodamine isothiocyanate; 2, 4-dinitrofluorobenzene, phenylisothiocyanate, dansyl choloride, substituted rhodamine isothiocyanates ("XRITC"), tetraethyl rhodamine isothiocyanate ("TRITC"), and phycobiliproteins (e.g,., allophycocyanin, HDITCP (1, 1', 3.3.3', 3' hexamethyl- 4,4', 5.5' dibenzo-2.2' indotricar bocyanine percholoate), and phycoerythrin) fluorophores, discussed in U.S. Pat. No. 4,877,965, which is incorporated herein by reference.

Preferably, the reference fluor is the same molecule as the signal fluor; the reference thereby gives a measure of the receptor integrity. In this case, it is required that signals from the bound and the free receptors are optically distinguishable. For example, when the signals are fluorescent, the optical property differences may be in emission wavelength, in excitation wavelength, in fluorescence lifetime, in polarization, in phase, or in combinations thereof However, when the reference fluor is a separate molecule, it can still correct for variations in illumination intensity and light path but can only indirectly correct for sensor particle aging due to photo-bleaching.

The sensor particle of the present invention may be a hydrophilic particle such as, but not limited to, controlled pore glass (CPG) beads or a polymer gel. It may also be a hydrophobic particle with appropriate plasticizers to permit free permeation by small analytes. Alternatively, it may be a semipermeable membrane such as, but not limited to, a liposome. To avoid the degradation of the receptor, the receptor may be bound to the inside of a hydrophilic particle, such as pores of CPG beads or a polymer gel. The receptors may also be captured inside a hydrophobic particle with appropriate plasticizers to permit free permeation by small analytes. The receptor may further be packaged inside the semipermeable membrane. For the purpose of the present invention, a plasticizer is appropriate if it permits free permeation of small analytes into a hydrophobic particle. Examples of such a plasticizer include, but are not limited to, Dioctyl Adipate, Diisodecyl Adipate, and the like. In accordance with an alternative embodiment, a receptor of the present invention may also be bound to the surface of hydrophobic or other insoluble particles.

The particle sensors of the present invention are in a size that prevents their encapsulation by scar tissues. Preferably, the particle sensors are built on the same scale as cells in the body. In an embodiment of the present invention, the sensor particles are in a size range from about 1–10 micrometers.

The particles are preferably round and uniform, such as commonly available polystyrene latex particles formed by emulsion polymerization. They may be produced of other materials and by other processes that are known in the art. Examples of the materials and methods include, but are not limited to, plasticized polyvinyl chloride (PVC) particles produced by droplet casting of dissolved polymers or glasslike particles produced from sol gels. In addition, the sensor particles may be made of a bio-resorbable polymer. Examples of a bio-resorbable polymer include, but are not limited to, polyglycoic acid (PGA), poly-DL-lactide-co-glycolide (PLGA), starch, gelatin, and the like.

The sensor particles of the present invention may be placed into the skin by any method that allows the sensor particles to be in contact with the interstitial fluid. For example, the sensor particles may be tattooed to the skin. If the sensor particles are made of bio-absorbable materials, they may be placed in contact with the skin under a condition that allows the skin to absorb the bio-absorbable polymer into the skin.

Once the sensor particles are placed in contact with the interstitial fluid, a laser light source may be used to emit laser light for exciting signal fluors. A laser light source can be a near-infrared (NIR) laser, a visible light laser or ultraviolet laser, although the NIR laser is preferred. In a preferred embodiment laser diodes are used as a light source since they are inexpensive, compact, high-intensity sources of exciting light for signal fluors of the present invention. Commercially available laser diodes that are suitable for use in the present invention include, but are not limited to the diode laser sold by Toshiba America Electronics Components, Inc. as Model Numbers TOLD9211F and TOLD9441MC.

The invention uses an external meter to detect analyte and reference signals. This meter may be held continuously in proximity to the skin overlying the sensor particles or, more preferably, it may be brought into such proximity at such time as analyte determinations are desired. The analyte and reference signals may be detected by methods commonly known in the art, once a sensor particle of the present invention is placed into the skin and the sensor particle is in contact with the interstitial fluid. In accordance with one embodiment of the present invention, an external meter shines light onto the skin and collects returned light from the skin. This returned light includes components backscattered by the tissue and by the particles, plus a portion of the signal and reference light produced by the particles. The meter measures the returned portion of signal and reference light by methods commonly known in the art, such as the use of wavelength selective filters, phase sensitive detection, or time gated detection. The meter may take multiple measurements of signal and reference light during a single determination, thereby reducing the effects of random fluctuations and other noise sources. The meter may combine the measurements of signal fluorescent light with the measurements of reference fluorescence light to correct for variations in illuminating intensity, overlying tissue optical density, fluor aging, and the like. One example of such a meter includes: a source, preferably a laser diode; a pair of detectors such as photomultiplier tubes, avalanche photodetectors. or photodiodes; a pair of optical filters, each associated with one of the detectors, to separate the emitted fight by wavelength; a collection optics to direct received light through the filters and onto the photodetectors; and a controller to determine levels based on the strength of the measured signals.

In order that the meter may be properly aligned with that region of the skin which overlies the sensor particles, it is desirable that the region be marked so that the user may readily locate it. Such marking can be applied with a surface marker, such as a pen, or the marking may be applied as part of the sensor implant. The receptor molecules themselves may act as a markers but it is expected that this will not prove adequate given the limited quantity of receptor molecules implanted and the preferred near IR wavelengths. The particles may be attached to or loaded with a more readily visible dye or pigment, or they may be co-implanted with other particles attached to or loaded with such a dye or pigment.

Periodically, the sensor particles are replaced with new particles. The sensor particles must be periodically replaced as they age due to photo-bleaching, to resorption by the body, or to other degradation processes. Replacement of sensor particles may be carried out by a health care professional.

Figure 4:
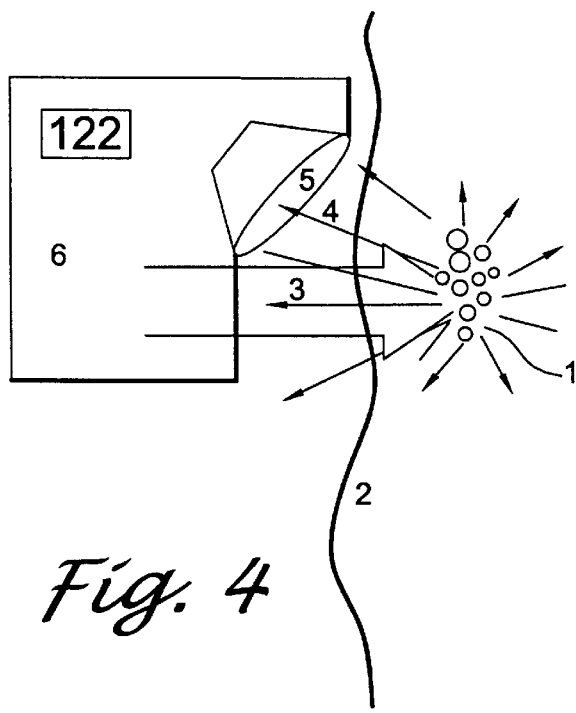
FIG. 4 is a diagram depicting components that may be used to implement a method of the present invention.

FIG. 4 is a diagram depicting components that may be used to implement a method of the present invention. In FIG. 4, sensor particles I are implanted into the skin 2. After the implantation, excitation light 3 is transmitted through the intervening skin portions from outside of the body to excite the signal fluors contained in the sensor particles. As a result, signal light 4 is emitted by the sensor particles in response to the excitation light. A portion of the signal light 4 is detected by detection optics 5 for measuring a portion of the signal light transmitted through the intervening portions of the skin. An analysis unit 6 is used for converting the signal light measurements into determinations of glucose concentration.

Figure 5:
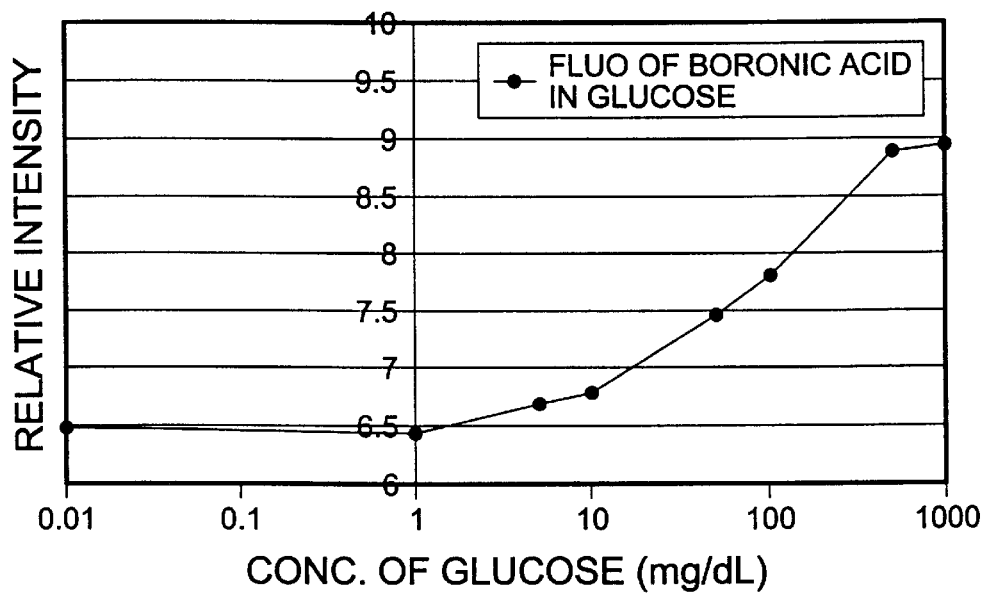
FIG. 5 is a plot of the fluorescence of a solution of the glucose receptor molecule against glucose concentration across the physiological range.

FIG. 5 is a plot of the fluorescence of a solution of the glucose receptor molecule of FIG. 2 against glucose concentration across the physiological range. The glucose receptor molecule is dissolved in diluted, glucose-depleted caprine serum as a simulant for the interstitial milieu. FIG. 5 demonstrated that the glucose concentration of the interstitial milieu may be determined by measuring the fluorescence intensity of the signal fluors associated with glucose receptor molecules.

The foregoing is meant to illustrate, but not to limit, the scope of the invention. Indeed, those of ordinary skill in the art can readily envision and produce further embodiments, based on the teachings herein, without undue experimentation.

The present invention may be embodied in other specific forms without departing from its essential characteristics. The described embodiment is to be considered in all respects only as illustrative and not as restrictive. The scope of the invention is, therefore, indicated by the appended claims rather than by the foregoing description. All changes which come within the meaning and range of the equivalence of the claims are to be embraced within their scope.

What is claimed is:

1. A method for detecting an analyte contained in the interstitial fluid of a body comprising the steps of:
   (a) providing at least one sensor particle comprising a substance with a receptor and a signal fluor, wherein the receptor preferentially recognizes the analyte, and the binding of the receptor to the analyte makes the substance to undergo a photoinduced electron transfer (PET) whereby a detectable analyte signal is generated in response to the analyte concentration of the body, wherein the sensor particle is selected from the group consisting of: a hydrophilic particle with the receptor bound to the inside of the particle, hydrophobic particle with the receptor captured inside the particle, and hydrophobic insoluble particle with the receptor coupled to the surface of the particle;
   (b) placing the sensor particle into the skin of the body for allowing the sensor particle to be in contact with the interstitial fluid of the body to undergo a PET and to generate the detectable analyte signal;
   (c) detecting the generated analyte signal; and
   (d) determining the concentration of the analyte contained in the interstitial fluid.

2. The method of claim 1, wherein the analyte is glucose and the concentration of the glucose in the interstitial fluid is determined as a measurement for blood glucose of the body.

3. The method of claim 1, wherein the sensor particle further comprises another substance capable of generating a detectable reference signal such that the detectable reference signal is generated by the substance when the sensor particle is placed into the skin of the body.

4. The method of claim 1, wherein the receptor is isolated from the skin interstitial milieu of the body.

5. The method of claim 1, wherein the sensor particle comprises a hydrophilic particle, and wherein the receptor is bound to the inside of the hydrophilic particle.

6. The method of claim 5, wherein the hydrophilic particle is a CPG glass bead or a polymer gel, and the receptor is bound to the inside of the pores of the CPG glass bead or the pores of the polymer gel.

7. The method of claim 1, wherein the sensor particle comprises a hydrophobic particle with appropriate plasticizers to permit free permeation by small analytes, and wherein the receptor is captured inside the hydrophobic particle.

8. The method of claim 1, wherein the sensor particle comprises a hydrophobic insoluble particle, and wherein the receptor is coupled to the surface of the hydrophobic insoluble particle.

9. The method of claim 1, wherein the size of the sensor particle is in the range of from about 1 to about 10 microns.

10. The method of claim 1, wherein the sensor particle is in a uniform shape.

11. The method of claim 1, wherein the sensor particle is in a round shape.

12. The method of claim 1, wherein the sensor particle is made from a material selected from a group consisting of polystyrene latex particles, plasticized polyvinyl chloride particles, glass-like particles, a semipermeable membrane, and a bio-resorbable polymer.

13. A method for detecting an analyte contained in the interstitial fluid of a body comprising the steps of:
   (a) providing at least one sensor particle comprising a substance capable of undergoing a photoinduced electron transfer (PET) and generating a detectable analyte signal in response to the analyte concentration of the body;

(b) placing the sensor particle into the skin of the body by tattooing technique, whereby the sensor particle is contacted with the interstitial fluid of the body to undergo a PET and to generate the detectable analyte signal;

(c) detecting the generated analyte signal; and (d) determining the concentration of the analyte contained in the interstitial fluid.

14. The method of claim 1, wherein, in step (c), the signal is a fluorescence signal and the fluorescence signal is detected by illuminating the signal fluor with a near-infrared wavelength.

15. The method of claim 1, wherein the body is a body of a vertebrate animal.

16. The method of claim 15, wherein the body is a human body.

17. A method for detecting an analyte contained in the interstitial fluid of a body comprising the steps of:

(a) providing at least one sensor particle comprising at least two different types of receptors with signal fluors, wherein the receptors preferentially recognize the analyte;

(b) placing the sensor particle into the skin of the body for allowing the sensor particle to be in contact with the interstitial fluid of the body to bind analyte and undergo a photoinduced electron transfer (PET) whereby a detectable analyte signal generated in response to the analyte concentration in the body;

(c) detecting the generated analyte signal; and (d) determining the concentration of the analyte contained in the interstitial fluid.

18. The method of claim 17, wherein the sensor particle comprises a semipermeable membrane, and the receptor is packaged inside the semipermeable membrane.

19. The method of claim 18, wherein the semipermeable membrane is a liposome.

20. The method of claim 17, wherein the analyte is glucose, the receptor preferentially recognizes the glucose, and the receptor is a diboronic acid conjugated to the signal fluor.

21. The method of claim 20, wherein the diboronic acid is N,N'-Bis(2-boronylbenzyl)-3,3,3',3'-tetramethylindolinium chloride or 9,10-Bis[N-methyl-M-(o-boronobenzyl)amino]methyl]anthracene.

22. A method for detecting an analyte contained in the interstitial fluid of a body comprising the steps of:

(a) providing at least one sensor particle comprising a first substance capable of generating an analyte signal that is responsive to the analyte concentration of the body and a second substance capable of generating a reference signal that is independent of the analyte concentration of the body, wherein the first substance is a collection of different receptors with signal fluors and the receptors preferentially recognize the analyte;

(b) placing the sensor particle into the skin of the body for allowing the sensor particle to be in contact with the interstitial fluid of the body to generate the detectable analyte signal;

(c) detecting the generated analyte signal; and (d) determining the concentration of the analyte contained in the interstitial fluid.

23. The method of claim 22, wherein the analyte is glucose, and the receptors preferentially recognize the glucose, and at least one receptor is diboronic acid conjugated to the signal fluor.

24. The method of claim 10, wherein the diboronic acid is N,N'-Bis(2-boronylbenzyl)-3,3,3',3'-tetramethylindolinium chloride or 9,10-Bis anthracene.

25. The method of claim 22, wherein the second substance is a signal fluor molecule.

26. The method of claim 22, wherein, in step (d), the analyte concentration is determined by comparing the analyte signal to the reference signal.

27. The method of claim 22, wherein the sensor particle is made from a material selected from a group consisting of polystyrene latex particles, plasticized polyvinyl chloride particles, glass-like particles, a semipermeable membrane, and a bio-resorbable polymer.

28. A method for detecting an analyte contained in the interstitial fluid of a body comprising the steps of:

(a) providing at least one sensor particle comprising a substance capable of undergoing a photoinduced electron transfer (PET) and generating a detectable analyte signal in response to the analyte concentration of the body, wherein
the sensor particle is made of a bio-resorbable polymer, wherein the bio-resorbable polymer is selected from a group consisting of polyglycoic acid (PGA), poly-DL-lactide-co-glycolide (PLGA), starch, gelatin, and the like;

(b) placing the sensor particle into the skin of the body for allowing the sensor particle to be in contact with the interstitial fluid of the body to undergo a PET and to generate the detectable analyte signal;

(c) detecting the generated analyte signal; and (d) determining the concentration of the analyte contained in the interstitial fluid.

29. A method for detecting an analyte contained in the interstitial fluid of a body comprising the steps of:

(a) providing at least one sensor particle comprising a receptor with a signal fluor, wherein the receptor preferentially recognizes the analyte, and the receptor that is bound to the analyte is a bound receptor and the receptor that is not bound to the analyte is a free receptor;

(b) placing the sensor particle into the skin of the body for allowing the sensor particle to be in contact with the interstitial fluid of the body, whereby the signal fluor contained in the bound receptor generates an analyte signal that is responsive to the concentration of the analyte contained in the interstitial fluid, the signal fluor contained in the free receptor generates a reference signal that is distinguishable from the analyte signal;

(c) detecting the generated analyte signal and the reference signal; and (d) determining the concentration of the analyte contained in the interstitial fluid.

30. The method of claim 29, wherein in step (d), the analyte concentration is determined by comparing the analyte signal to the reference signal.

31. The method of claim 29, wherein the sensor particle is made from a material selected from a group consisting of polystyrene latex particles, plasticized polyvinyl chloride particles, glass-like particles, a semipermeable membrane, and a bio-resorbable polymer.

* * * * *